United States Patent [19]
Brackett

[11] Patent Number: 5,904,655
[45] Date of Patent: May 18, 1999

[54] DISPOSABLE BLOOD PRESSURE COVER AND METHOD FOR UTILIZING THE SAME

[76] Inventor: Jacqueline D. Brackett, 8255 Brackett La., Semmes, Ala. 36575

[21] Appl. No.: 08/881,326

[22] Filed: Jun. 24, 1997

Related U.S. Application Data

[60] Provisional application No. 60/020,900, Jun. 27, 1996.

[51] Int. Cl.[6] .................................................. A61B 5/02
[52] U.S. Cl. .................................... 600/490; 600/499
[58] Field of Search .......................... 600/485, 490–499, 600/500; 128/853–856; 606/202–203; 224/901, 901.2, 901.5, 901.8

[56] References Cited

U.S. PATENT DOCUMENTS

| | | | |
|---|---|---|---|
| 4,548,249 | 10/1985 | Slaughterbeck | 600/499 X |
| 4,967,758 | 11/1990 | Masciarotte | 600/499 |
| 5,228,448 | 7/1993 | Byrd | 600/490 |
| 5,620,001 | 4/1997 | Byrd et al. | 600/490 X |
| 5,651,368 | 7/1997 | Napolitano et al. | 600/490 |

*Primary Examiner*—Brian Casler
*Assistant Examiner*—Ryan Carter

[57] ABSTRACT

A semi-disposable blood pressure cuff system is disclosed utilizing a sheet of cuff or bladder covers. The two-fold function is: to provide a protective covering for an existing blood pressure cuff or pneumatic tourniquet cuff and functions as the disposable member of a semi-disposable blood pressure cuff system. The cuff cover has a width and length of adequate dimension to cover and protect the functional cuff and is also of adequate size that, when paired with the commercially available cuff inflation bag, can function by itself as a blood pressure cuff. This allows the user to construct a new blood pressure cuff for use on each patient. The method disclosed is designed to protect the public from a known carrier of disease, i.e. the reusable blood pressure or tourniquet cuff. The packaged roll is perforated at designated lengths that correspond to the length of one cuff saver unit so that the user may tear away the desired unit for use much in the same way one tears away a paper towel from it's dispensing roll. Each unit is equipped with adhesive fastening devices along one edge of it's running length and also a patch of adhesive fastening according to the design specifications of that particular size unit.

20 Claims, 4 Drawing Sheets

DISPOSABLE BLOOD PRESSURE COVER AND METHOD FOR UTILIZING THE SAME

PRIORITY STATEMENT

This is a continuation in part of the provisional application Ser. No. 60/020,900 filed Jun. 27, 1996.

BACKGROUND OF THE INVENTION

This invention relates to blood pressure cuffs. More particularly, the invention relates to blood cuff cover which forms half of a semi-disposable cuff system having a disposable cover and a reusable bladder. This has two basic functions: (a) to provide a disposable component of a semi-disposable pressure measurement system that allows the user to manufacture, for each patient, a new clean cuff and (b) to provide a disposable cover capable of protecting an existing cuff from contamination.

PRIOR ART

The closest known prior art is U.S. Pat. No. 4,548,249 to Slaughterbeck which suggests the use of replaceable protective sleeves for Blood Pressure Cuffs. This design is configured with removable sections that are meant to provide exposure of the fastening on the reusable cuff.

U.S. Pat. No. 5,228,448 to Byrd suggests a limb drape that is wrapped about the patient's limb at the time of use. The reusable blood pressure cuff is then wrapped about the area that the drape covers. After wrapping the cuff and securing it's fastenings, the remainder of the limb drape is brought over the cuff to cover it's surface. This device requires a greater level of patient cooperation while the drape is being placed and it consumes valuable time that might be spent for other patient care functions in times of emergency. This cover must also be left on the patient's arm for repeated use since it does not function once removed.

GENERAL DESCRIPTION OF THE INVENTION

The disclosed covers are intended for two functions. The first function is to provide a protective covering for blood pressure cuffs or bladders. This protective covering would protect the patient from the potential pathogenic organisms that the cuff itself might harbor and would protect the cuff from soiling and contamination that can occur during patient contact. The covers are disposable. This would provide the public with a safe and more cost effective blood pressure and tourniquet cuff. The second function is that the cuff cover can be used in conjunction with a commercially available inflation bag/bladder as a blood pressure cuff system that should provide the public with a cost effective and sanitary alternative to the conventional blood pressure cuff used in today's health care industry. This would be, in effect, a semi-disposable single patient use system that would be extremely cost effective and sanitary due to the fact that the cuff saver is made of inexpensive Non-woven fiber it is designed for single patient use and the reusable bladder can be thoroughly and rapidly sanitized and dried due to the nonporous nature of it's surface. This would eliminate the need for health care institutions to have on hand a large supply of cuffs that have to be cleaned or sterilized between patient use.

The cuff cover disclosed herein is known by the trademark "Cuff Saver™". The unit consists of a sheet of non-woven fiber with a length that is typically greater than it's width. The length is standard for the size cuff to be used: infant, toddler, child, small, regular, large, and thigh. The width is typically greater than double the standard size and should be adequate to fold over the cuff or bladder and cover it completely. It is also of adequate size so that when folded in half, it is the width of the standard size cuff to be used. Along the running distal width edge is a strip of adhesive that will secure the Cuff Saver™ over the cuff or inflation bag/bladder when the Cuff Saver™ is folded down over the cuff or inflation bag/bladder. There may also be a patch of adhesive fastening at the proximal half of the cuff saver for adhering the bladder to the inside surface of the Cuff Saver™. Adhesives in this patent may be replaced with cooperating hooks and loops and the like. Once the Cuff Saver™ is folded over, this reveals the outside surface of the Cuff Saver™. The Cuff Saver™ may then be turned over to reveal the inner surface of the Cuff Saver™. This is the surface that will make contact with the patient's skin. It contains the printed instructions, reference lines, and size labeling. This side also has a patch of adhesive fastening for securing the cuff device to it's own surface. This adhesive has the property of being reusable for multiple applications of the cuff without damaging the structural integrity of the Cuff Saver™.

This allows the user to construct a new clean cuff for each patient use. This cuff may be constructed prior to patient contact, thus saving time needed for attending to the patient. The cuff cover may also be applied to the nondisposable cuff prior to patient contact. They are a disposable single patient use item and may be packaged as a single unit or on manufactured rolls of a designated number of units per roll. The pneumatic tourniquet cuff version may be backed with a soft cotton batting or other suitable material so that eh pressure of the pneumatic cuff does not produce undo compression against the patient's skin. Each unit may be printed with instructions pertaining to the use of the device, other necessary information, and possibly a decorative design. They will be manufactured out of medical grade Non-woven fiber that is fluid resistant and feels soft to the touch.

It is therefore the purpose of this invention to provide a safer more sanitary method of protecting a bladder or blood pressure cuff from soiling. Further, it is the purpose of this invention to provide a unique cuff cover system that may be removed between same patient use without destroying the integrity of the cover itself. It is also the purpose of this invention to describe a unique method of dispensing a semi-disposable cuff utilizing the disposable component of the system and the commercially available cuff inflation bag/bladder as the reusable component. Further, this method describes a disposable cuff that may be removed and reused on the same patient and a cuff cover that allows the blood pressure cuff to be removed without destroying the cover itself.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein.

DETAILED DESCRIPTION OF PREFERRED EMBODIMENT

Figure 1:
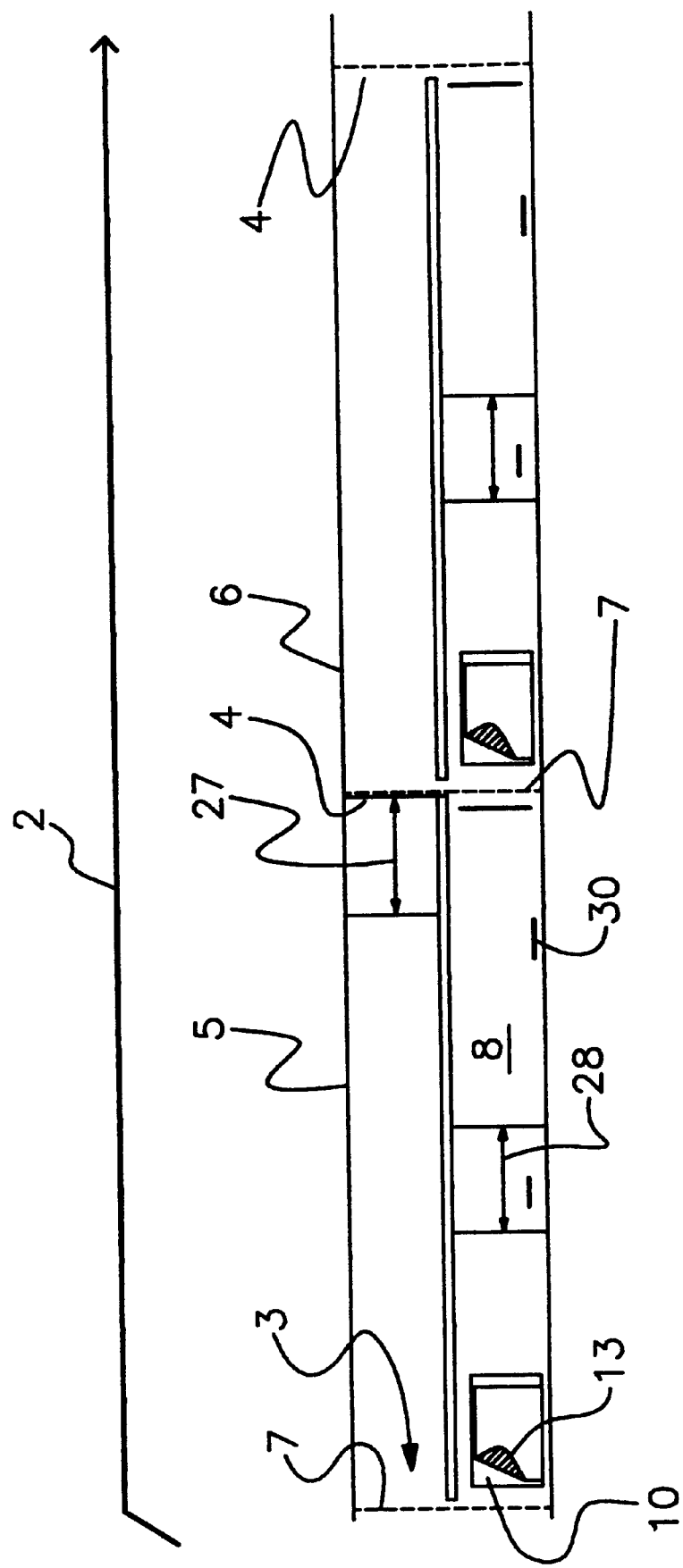
FIG. 1 is a perspective view of the preferred embodiment from the top.

As can best be seen by reference to FIG. 1, the invention in the preferred embodiment comprises a continuous sheet 2 of covers 1 wherein each cover 1 has a leading edge 3 and trailing edge 4 connecting the first cover 5 to the following cover 6. At the trailing edge 4 of the first cover 5 is the leading edge 3 of the following cover 6.

The first cover 5 and the following cover 6 are connected together by a third connecting means which in the preferred embodiment is a serrated edge 7. This serrated edge 7 allows for the first cover 5 to be torn free of the following cover 6. The covers 5 and 6 may be connected by tape, cooperating hooks and loops or any other joining mechanism. However, by having the serrated edge 7, the covers may be manufactured in rolls or folded stacks and more easily dispensed.

Figure 2:
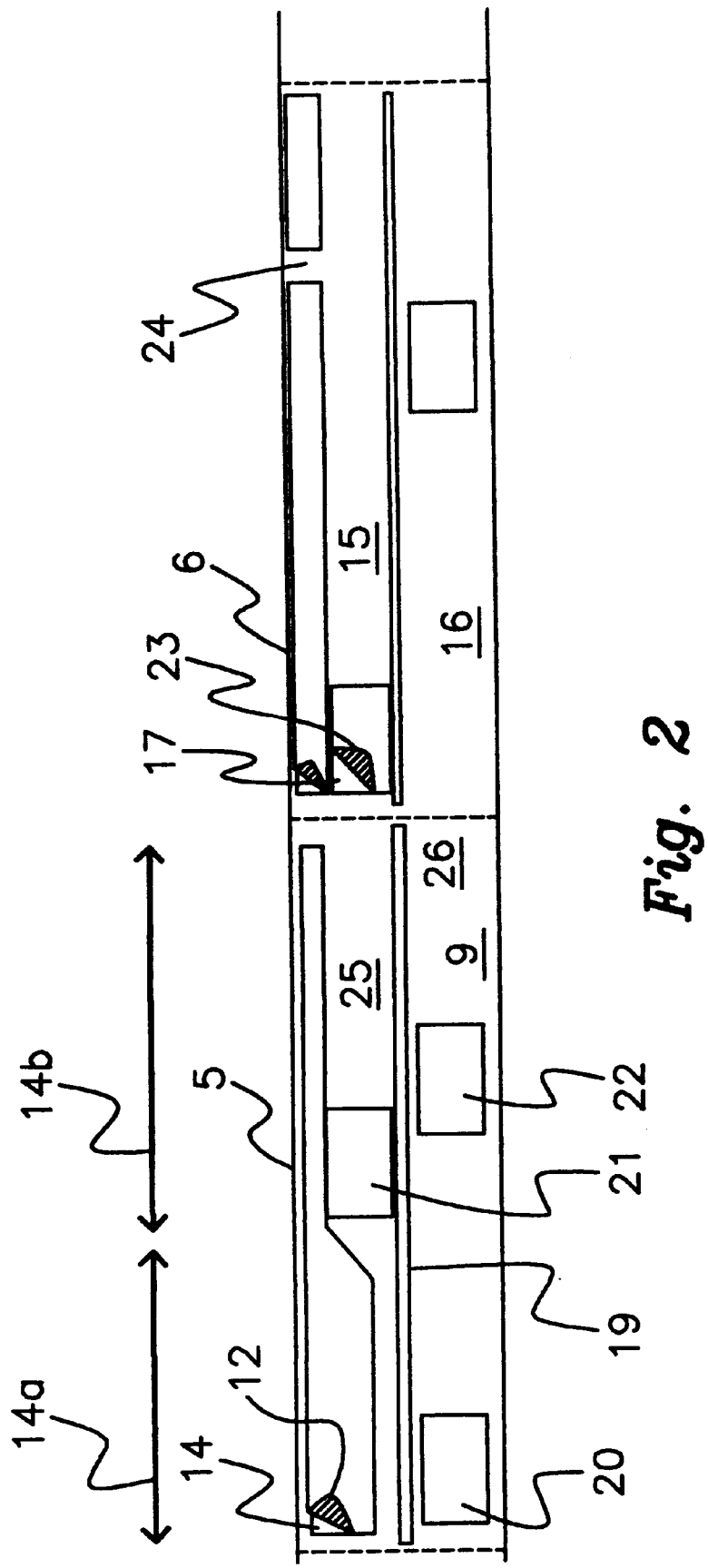
FIG. 2 is a perspective view of the preferred embodiment shown in FIG. 1 from the bottom.

Each cover has a top 8 shown in FIG. 1 and a bottom 9 shown in FIG. 2, wherein one is on the opposite side of the other. Hence, if one flipped the top 8 over, one would be looking at the bottom 9, and vice versa.

The top 8 has, at the leading edge 3, a first connecting means which is, in the preferred embodiment, a double-sided adhesive patch 10, which is approximately five inches by six inches. The double sided adhesive patch may be a layer of glue, so that the term double sided is for descriptive purposes only. One side is adhesive so as to stick to the top 8 and the other side of the double-sided adhesive patch is designed so as to stick to the binding location 27 on the cover 1 as described in more detail below. In the preferred embodiment, this double sided adhesive patch 10 is covered with a patch cover 13.

When the cover 1 is wrapped around the arm of the user, the patch 10 is aligned with the binding location 27. The patch cover 13 is removed and the cover is fixed in place on the user. The adhesive used in the patch 10 is preferably of a type which can fixed in place, pulled lose and re-affixed. Cooperating hooks and loops would serve this function as long as the hook or loops were located at the shown location for patch 10 and at the shown location for the binding location 27.

As shown in FIG. 1 there is a cover 13 for the first connecting means 10 which may be peeled away to reveal a five inch by six inch double-sided adhesive patch. Referring to the opposite side, shown in FIG. 2, which is the bottom 9 of the cover 1 there is a second connecting means which is preferably a double sided tape 14 which may run along the entire length of the cuff cover. The double sided adhesive patch may be a layer of glue, so that the term double sided is for descriptive purposes only. This double sided tape 14 may be wise 14a enough so as to attach to both the bladder 11 (not shown) so as to hold the bladder 11 in place and may then become thin 14b enough so as to only serve to adhere to cap 25 to the base 26 when the cover 1 is folded along fold 19. The following cover 6 is shown with a single width tape 14. However, this single width tape 14 is shown with a fourth connecting means, here bladder glue 17 which can be used to secure the bladder 11 in place. Both the double sided tape 14 and the bladder glue 17 have a tape cover strip 12 and the glue cover 23 respectively.

This second connecting means, tape 14 may have breaks 24 along its length in order to accommodate hoses which may run from the bladders which are used in the art of bladders and cuffs.

In use, the first cover 5 is separated form the following cover 6 by tearing the serrate edge 7. The tape cover 12 is removed and a bladder is put in place (either being affixed to the widened location 14a of the tape 14, by placing on the glue 17 or by placing the bladder without any attachment means) then the left side 15 of the bottom 9 is folded over to meet the right side 16 of bottom 9 when the two are sealed together. The hoses are left extending out of this arrangement, possibly at breaks 24 in the tape 14 provided for this purpose.

A strip 12 covers the adhesive strip second connecting means, tape 14 so that the invention may be practiced.

The cover 1 has a size area for placing the index line 29 so that it is properly sized. There is also an artery location 30 for alignment purposes which is preferably at the location opposite the break 24 where the bladder liens come out.

Opposite these markings 27, 28, 29, 30 is a part of the cover 1 which may be used for various displays (the name of the hospital, written identification of the patient, specific readings or other nurses notes, etc.).

Opposite, there are a first tear away 20, a second tear away 21, a third tear away 22, and a fourth tear away 23 which may be removed to expose the bladder or other parts of the interior formed by folding the cover 1 to the exterior to the extent desirable. These tear aways are possible by virtue of perforations in the surface of the cover 1, shown as the perimeter of the tear away 20, 21 and 22. The main purpose of these where present would be to expose velcro in the underlying cuff so that the cuff's attachment mechanism could be used. Generally this would not be desirable and the tear aways would not be present in the preferred embodiment.

Figure 3:
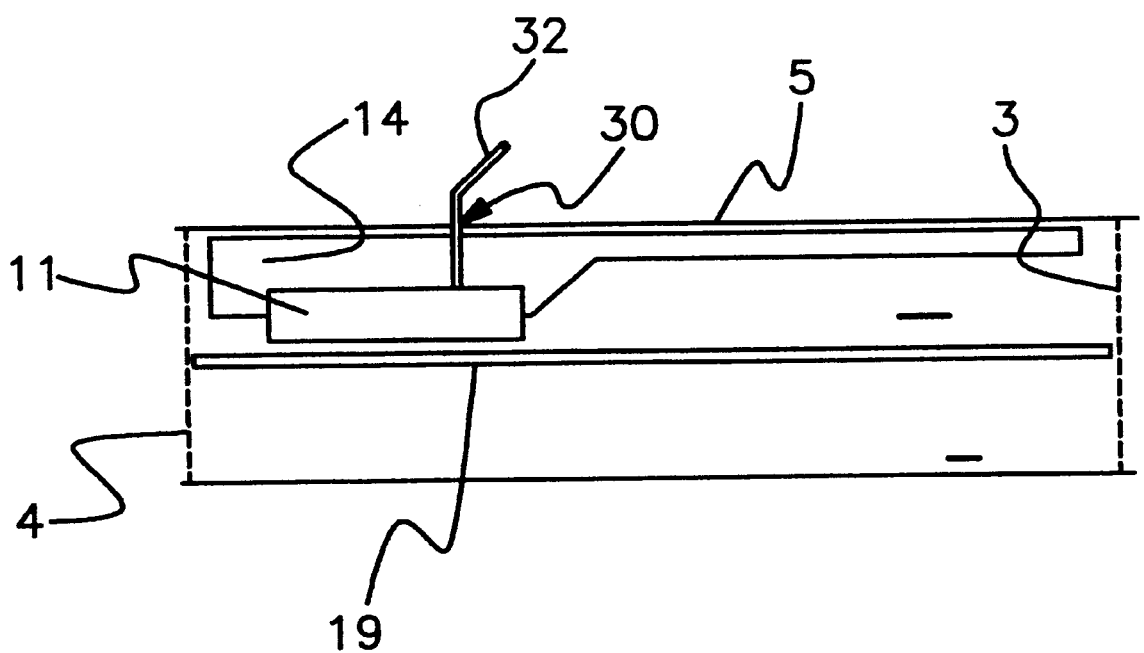
FIG. 3 is an individual cover from FIG. 1 shown with a bladder in place.
Figure 4:
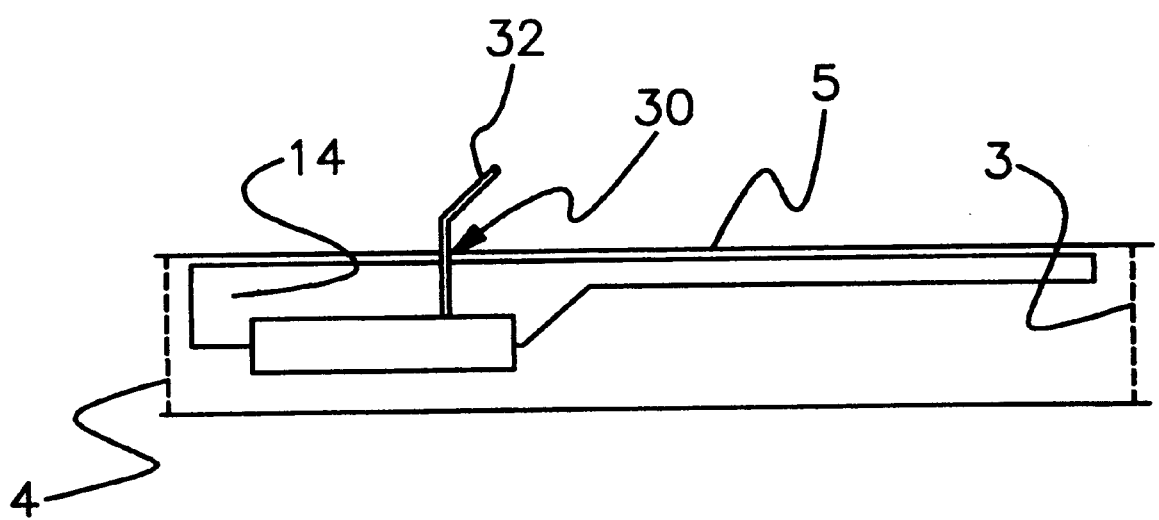
FIG. 4 is the cover from FIG. 3 after it is sealed.

Once the cover is assembled over the bladder, the patch cover 13 is removed and the cover may be placed on the patient in a manner identical to existing blood pressure cuffs. The cuff saver may be used in the following process:

1) tearing away one Cuff Saver™ from the dispensing roll or open an individually packaged unit forming a continuous sheet;
2) placing the unit printed side or top down on a level surface;
3) peeling away the paper strip 12 covering the adhesive patch or tape 14 located on the cap 25 (preferably the proximal half of the unit). This tape 14 is an adhesive edge which is glue or tape or other attachment means;
4) placing the cuff or inflation bag/bladder on the proximal half of the unit with the top of the cuff or inflation bladder at the fold 19 which is preferably marked "Fold Line" as shown in FIG. 3 (Alternatively, the bladder may be centrally located over the exposed adhesive or on a special bladder glue 17); and
5) pressing into place the base 26 onto the exposed tape 14 on the cap 25. The inflation tubing 32 of the cuff or inflation bag/bladder now extends from the unit at the area marked "Artery" known as the artery location 30. The outer surface should now be visible as shown in FIG. 4;
6) turning the unit over and note the printed index and reference lines for sizing the unit. The unit may then be applied as one would apply an ordinary cuff to the patient's limb;
7) wrapping the cuff securely and the area of the large adhesive patch is reached;

8) peeling away the paper patch cover 13 backing on the patch 10 and the exposing the adhesive of the patch 10;

9) continuing wrapping the cuff until the revealed adhesive secures the unit to itself.

As shown in FIG. 4, where a permanent adhesive is used for the first connecting means, there may be a tear away section 31 in the middle of the cover 1 for tearing the cover 1 so that it may be removed. In the preferred embodiment, the first connecting means is a reusable glue so that the cuff may be reused on the same patient and then disposed of only when the patient no longer requires the cuff or when it becomes to soiled to continue using with replacement of the cover 1.

Because many varying and different embodiments may be made within the scope of the inventive concept herein taught and because many modifications may b made in the embodiment(s) herein detailed in accordance with the descriptive requirements of the law, it is to be understood that the details herein are to be interpreted as illustrative and not in a limiting sense.

What is claimed is:

1. A series of individual cuff covers followed by following covers said cuff covers for enclosing an air bladder having a leading edge and a trailing edge and a fold separating the cuff cover into a cap and a base, wherein the trailing edge of each cuff cover attaches removably from the leading edge of the following cover and wherein each cuff cover further comprises a top and a bottom, and wherein said top further comprises a cap and a base and wherein said cuff cover top further comprises at least one first connecting means and wherein the bottom of said cuff cover comprises at least one first connecting means and wherein the bottom of said cover comprises at least one second connecting means 14 along the left side of said bottom so that when the cuff cover is folded along the fold so that the cap of the bottom faces the base of the bottom the second connecting means serves to secure the cap of the cuff cover to the base of the cuff cover.

2. The cuff cover of claim 1 wherein the first connecting means further comprises a cuff cover which serves to protect the first connecting means until it is ready for use.

3. The cuff cover of claim 2 wherein the first connecting means comprises glue.

4. The cuff cover of claim 1 wherein the second connecting means further comprises a strip which serves to protect the second connecting means until it is ready for use.

5. The cuff cover of claim 4 wherein the second connecting means comprises glue.

6. The invention of claim 1 wherein said cuff cover further comprises a bladder attachment means for holding the bladder in place on the cuff cover.

7. The invention of claim 6 wherein the bladder attachment means further comprises glue.

8. The invention of claim 7 wherein the bladder attachment means further comprises bladder cover for covering the glue until it is ready for use.

9. The invention of claim 7 wherein the bladder attachment means is an extension of the second connecting means.

10. The invention of claim 1 wherein the cuff cover further comprises at least one third connecting means for joining the cuff cover to at least one following cover so that a continuous sheet of cuff covers is formed.

11. The invention of claim 10 wherein the third connecting means further comprises a common line of intersection between the trailing edge of the cuff cover and the leading edge of the following cover.

12. The invention of claim 11 wherein the third connecting means further comprises the common line of intersection being serrated.

13. The invention of claim 10 wherein the third connecting means further comprises an extension of the first connection means.

14. The invention of claim 1 wherein the first connecting means is a reusable glue.

15. The invention of claim 1 wherein at least one of the connecting means is in the form of double sided tape attached to the cuff cover on one side.

16. The invention of claim 15 wherein the double sided tape further comprises a tape cover so that when the cuff cover is rolled, the tape is covered.

17. The invention of claim 1 wherein the top further comprises a writing surface for applying notes relative to the operation of the cuff cover.

18. The invention of claim 1 further comprising a tear-away line running along the width of the cuff cover so that even if the tape remains sealed when the cuff bladder is removed, the cuff cover may be torn along the tear away line for easy removal along this tear-away section, which might preferably be the mid-point fold.

19. A process for maintaining sanitary blood pressure bladders comprising the steps of:

1) placing a cover having a cap, a base and a fold for the bladder on a surface;

2) placing the bladder on the base of the cover;

3) adhering the cover cap to the cover base so that the bladder is at least partially enclosed with the lines from the bladder extending out of the enclosure formed;

4) attaching the cover to patient so that the bladder is in place on the patient at the desired location;

5) removing the cover from the patient;

6) removing the bladder from the cover for reuse.

20. The invention of claim 19 wherein the step of adhering the cover cap to the base further comprises the steps of:

peeling away a strip 12 covering an adhesive patch located on the cap.

\* \* \* \* \*